United States Patent
Mbachu et al.

(10) Patent No.: US 7,468,155 B2
(45) Date of Patent: *Dec. 23, 2008

(54) SPECTROSCOPIC MONITORING OF RESIN-LOADING DURING ASSEMBLY OF ENGINEERED WOOD PRODUCT

(76) Inventors: Reginald A. Mbachu, 3950 Goodpasture Loop, Suite W112, Eugene, OR (US) 97401; Tyler G. Congleton, 2631 Windsor Cir. West, Eugene, OR (US) 97405

( * ) Notice: Subject to any disclaimer, the term of this patent is extended or adjusted under 35 U.S.C. 154(b) by 807 days.

This patent is subject to a terminal disclaimer.

(21) Appl. No.: 11/009,049

(22) Filed: Dec. 13, 2004

(65) Prior Publication Data
US 2005/0140037 A1 Jun. 30, 2005

Related U.S. Application Data

(63) Continuation-in-part of application No. 10/294,296, filed on Nov. 14, 2002, now Pat. No. 6,846,446.

(51) Int. Cl.
*B29C 45/76* (2006.01)

(52) U.S. Cl. ............. 264/406; 264/410; 264/488; 264/492; 264/40.1

(58) Field of Classification Search ............ None
See application file for complete search history.

(56) References Cited

U.S. PATENT DOCUMENTS

| | | | | |
|---|---|---|---|---|
| 3,196,072 A | * | 7/1965 | Wirtz | 162/198 |
| 5,619,038 A | * | 4/1997 | Parigi et al. | 250/339.12 |
| 6,461,743 B1 | * | 10/2002 | Tanzer et al. | 428/535 |

* cited by examiner

*Primary Examiner*—Monica A Huson (57) ABSTRACT

Calibrating visual (VIS) and near infra red (NIR) spectroscopic instrumentation for quantitative measurement of resin-loading of prepared wood materials, as moving in an assembly-forming line, for subsequent pressing under heat and pressure for manufacture of engineered-composite wood product. Feedback of measured data of resin-loading, during in-line assembly operations, enables maintaining consistent resin-loading and optimizes resin usage. Calibration of VIS/NIR spectroscopic instrumentation can be carried out on equipment simulating in-line movement of pre-established reference-source test-samples; or, can be carried out during on-line movement of wood-material test samples. The developed calibration method removes absorptive effects at wavelengths for constituents other than resin, such as the moisture content of the wood-materials and of the resin, while maintaining accurate and prompt VIS/NIR spectroscopic measurements of resin-loading in a continuous assembly line.

17 Claims, 7 Drawing Sheets

SPECTROSCOPIC MONITORING OF RESIN-LOADING DURING ASSEMBLY OF ENGINEERED WOOD PRODUCT

RELATED APPLICATION

The present application is a continuation-in-part of Ser. No. 10/294,296 filed Nov. 14, 2002, now U.S. Pat. No. 6,846,446 which is incorporated herein by reference.

INTRODUCTION

This invention relates to use of Visual (VIS) and near infrared (NIR) radiation and spectroscopic instrumentation for measuring resin-loading of wood-materials during assembly-line movement in order to achieve resin-loading results within manufacturing standards for subsequent production of composite wood product. In one of its specific aspects this invention is concerned with calibrating VIS and NIR spectroscopic instrumentation for quantitative analysis of resin-loading of wood-strand materials.

OBJECTS OF THE INVENTION

Objects of primary importance involve uncovering methods for using a selected range of visual (VIS) and near infrared (NIR) electromagnetic radiation and spectroscopic technology for quantitative measurement of resin-loading of wood-materials while traveling in-line for assembly of engineered wood product; so as:
  (a) to achieve homogeneity of engineered wood product,
  (b) to maximize production of engineered wood product within desired manufacturing specifications, and
  (c) to optimize resin usage.

A related important object involves calibration of VIS and NIR spectroscopic instrumentation to enable measuring resin-loading of wood-materials while being moved to simulate movement in a continuous-type assembly line.

A related object includes assembly-line resin-loading verification involving feed-back of resin-loading information as measured by calibrated VIS and NIR spectroscopic instrumentation so as to maximize continuity of assembly operations for subsequent production of composite wood-strand product within desired manufacturing specifications.

The above and other objects and contributions of the invention are disclosed in more detail during description of the invention in relation to the accompanying drawings.

DETAILED DESCRIPTION OF INVENTION

Analyzing problems associated with continuous-type assembly-line processing of wood materials and uncovering concepts for use of spectroscopy, including calibrating in a selected range of visual (VIS) and near infrared (NIR) spectroscopic instrumentation, contributed solutions capable of being carried out on-line to provide for quantitative measurement of resin-loading of wood-materials while moving in-line for assembly and subsequent pressing into composite wood product.

VIS/NIR spectroscopic quantitative analyses of resin-loading during in-line movement for assembling wood-materials into composite had been unknown; and, correlating aspects of line operations, by feedback of measuring results using calibrated VIS/NIR spectroscopic instrumentation, enabling quantitative resin-loading analyses during continuing-type in-line movement and assembly of wood-materials for subsequent pressing into composite wood product.

For purposes of disclosure of those concepts in more detail, a specific embodiment of the invention will be described involving resin-loading of multiple individual layers, each formed from wood-strand materials as described herein, is measured during in-line assembly for uniform results.

The non-invasive on-line quantitative measurements of resin-loading of the invention enables production of composite wood-strand product which is within desired manufacturing specifications; and, also, enables providing for on-line verification and control of resin-loading, which is significant in continuous-line assembly of wood-strand materials by contributing to uniform high-strength characteristics for oriented-strand products assembled, in accordance with the invention, as used for "I" joists, two-by-fours, other structural components, and for composite sheeting for floors, roofs and siding.

Use of the presently disclosed calibrated VIS/NIR spectroscopic measurements enables timely determination of resin-loading during continuing in-line movement of wood-materials as being assembled; and, for timely on-line modifications of resin-loading to maintain desired standards. The present principles of VIS/NIR spectroscopic measuring technology, during assembly, can also contribute to verification of desired resin-loading by measurements after heat and pressure bonding of composite-wood product.

Figure 1:
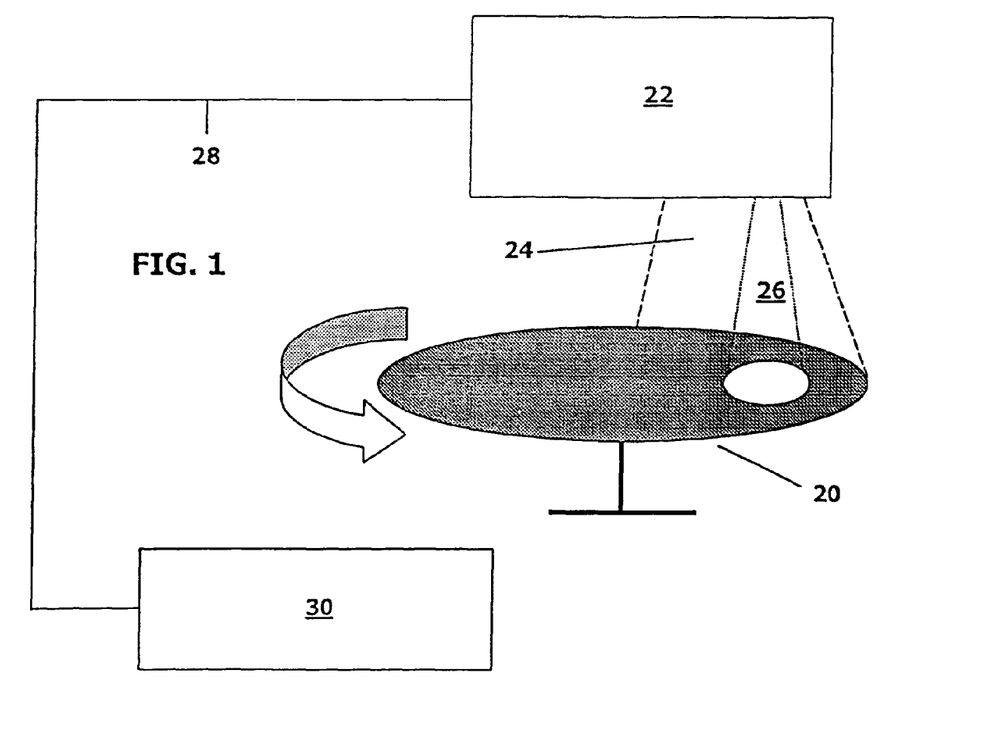
FIG. 1 is a schematic perspective view of an embodiment of the invention for calibrating VIS/NIR spectroscopic measuring instrumentation, and for training of those calibration principles.
Figure 2:
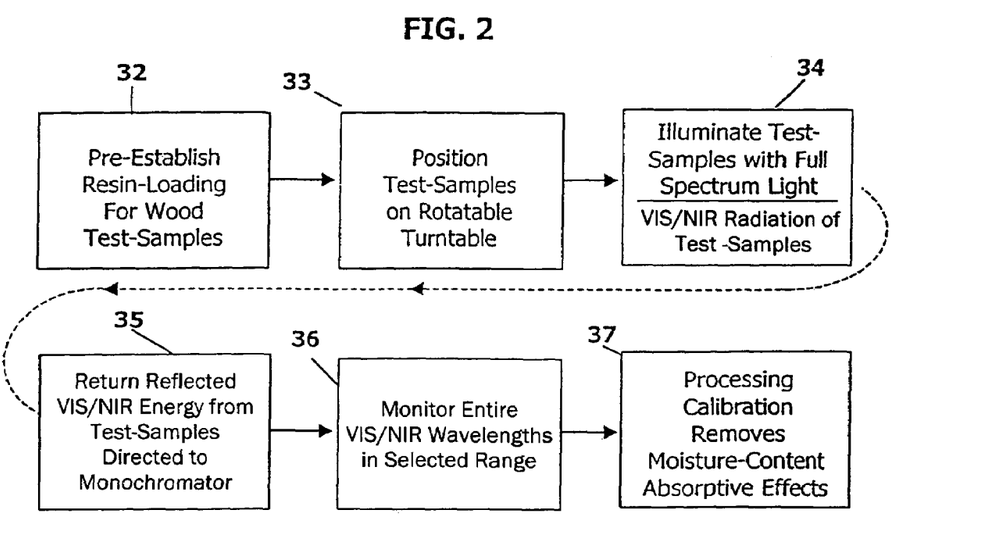
FIG. 2 is a diagrammatic presentation for describing steps in calibrating VIS/NIR spectroscopic measuring instrumentation in accordance with the invention.

FIG. 1 depicts apparatus for describing principles of the invention for calibrating in a selected range of visual (VIS) and near infrared (NIR) spectroscopic measuring instrumentation. Such apparatus can provide for accurate quantitative analysis of resin-loading under dynamic on-line assembly conditions; and, can be used for instruction, and training personnel for use of principles of the invention. The presentation of FIG. 2 is for describing steps for using those principles in accomplishing desired calibration of NIR spectroscopic instrumentation. And, FIG. 3 graphically depicts achievement of resin-loading results, within manufacturing standards, when using calibration principles of the invention for quantitative measurement of resin-loading using visual (VIS and near infrared (NIR) spectroscopy.

The apparatus of FIG. 1 can be used for calibrating VIS/NIR spectroscopic resin-loading measuring equipment off-line; or, for on-line calibration in a dynamic process in which wood-materials are moving in a continuing assembly line.

Calibration concepts of the invention are disclosed in relation to assembly of strand-wood materials. In a specific embodiment for assembly of oriented strand board (OSB), thin wood strands are cut from debarked and otherwise prepared logs. Those thin strands have widths of about 0.5 inch up to about two-inches, lengths of about four to about six inches, and thicknesses of about 0.02" to 0.025", as they are strand-cut or "flaked" for assembly of oriented strand board (OSB). A selected thermosetting adhesive-type resin is applied to those light-weight strands which are used in forming a plurality of individual strand layers, of selected thickness, for assembly of OSB. The multiple strand layers are subsequently bonded together using heat and pressure, into a unitary composite of wood-strand layers.

In calibrating the apparatus of FIG. 1 for quantitative analysis of resin-loading of strand-wood materials, such as thin wood strands, reference-source test-samples are first accurately pre-established in a specified order. Those reference-source test-samples, each presenting a pre-established resin-loaded layer of strand-wood material, are supported on a surface capable of providing movement at a selected controlled rate.

The test-samples of the embodiment of FIG. 1 are supported on turntable 20; and, turntable 20 is equipped to be capable of rotation so as to simulate an on-line controlled-rate of linear movement of resin-loaded strand-wood material. Preferably in the embodiment of FIG. 1, resin-loading of each individual reference-source test-sample is pre-established so as to produce incrementally differing resin-loaded percentage weights; for example, at levels from about 3% to about 12% resin-weight with respect to the weight of respective reference-source test-sample strand-wood material. Present principles can also be used in measuring resin-loading of wood-strand lumber in terms of spread-weight per unit area.

The test-samples are positioned on turntable 20 so as to be capable for a rate of movement which simulates a desired linear movement rate of resin-loaded wood-materials when carrying out measurement of resin-loading when carried out during assembly on-line. That is: rotation of turntable 20 of FIG. 1 enables correlation of test-sample movement with the prospective rate of movement of wood-materials on a conveyance surface used for assembly of the strand-wood materials traveling toward pressing apparatus bonding under heat and pressure.

Sensor head 22 includes a full-light spectrum lamp, for illuminating test-samples which is indicated by beam 24. In the specific embodiment, visual (VIS) and near infra-red (NIR) radiation source 26 provides for selecting of a desired range of radiation wavelengths within the full-scale wavelength region of about 350 to about 2500 nanometers (nm). A wavelength range, covering wavelengths from about 400 nm to about 2250 nm satisfactorily covers the above-mentioned full-scale region and is selected for providing desired penetration of wood-strand materials; and, for enabling quantitative analyses of resin-loading by measuring reflective VIS/NIR energy after absorption of VIS/NIR by the strand-wood material. Significantly, it has been determined that acceptable standards can be maintained by other than use of full-scale or near full-scale wavelength regions.

It has been found that selection can be made from multiple ranges of wavelengths. An individual wavelength range cam be selected from the following: (1) 350-1050 nm; (ii) 1000-1800 nm and (iii) 1000-2500 nm; those ranges and the type of sensors for measuring resin loading in each range are later described herein. The resulting advantages from discovery of those multiple ranges can be important in relation to the size of composite-wood manufacturing installations.

Penetrating VIS/NIR energy, in the selected wavelength spectrum, is at least partially absorbed by the resin-loaded wood-strand material. Non-absorbed VIS/NIR energy, as return-reflected by wood-materials on the conveyance surface, is directed via fiber-optic cable 28, for measurement, to monochromator 30.

The reflected radiation energy is measured in the selected range of wavelengths from 400 nm to 2250 nm; however, absorptive effects specific to moisture content of the strand-wood material and moisture content of the loaded resin, are preferably selectively removed in the processing of the spectra data at wavelengths of 900-1000 nm, 1400-1500 nm, and 1900-2000 nm. That calibration method provides for prompt computer determination of, and accurate quantitative analyses, of VIS/NIR absorption due to resin-loading of the wood-materials on the test-samples.

In a specific calibration embodiment, a thermosetting resin was accurately established for on OSB-strand wood test-samples, as indicated at stage 32 of FIG. 2; resin-loading percentage weight levels were established, as closely as practical, to approximately 3%, 6%, 9% and 12%. Differing moisture level wood strands were used in respective test-samples, in order to verify that differing moisture-content of the wood-material does not effect accurate resin-loading measuring ability. The results achieved in measuring said known resin-loaded test-samples verified the calibration method. The calibration for VIS/NIR spectroscopic quantitative analyses of resin-loading removes the absorptive effect of constituents other than resin; specifically, removing wavelengths of moisture-content of the strand-wood material and moisture content of the resin. That is accomplished, during processing as set forth above, by removing moisture-content peak absorptive effects in wavelength bands of 900-1000 nm, 1400-1500 nm, and 1900-2000 nm.

Rotating turntable 20 at twenty RPM with the sensor head NIR source lamp focused at a radius of ten inches from its center of rotation enabled simulating a selected linear rate of movement for use in forming wood strand layers in an assembly line. Position of sensor head 22 is preferably selected in a range of about four to about ten inches above the samples.

In the calibration steps of FIG. 2, the test-samples are positioned for support on a movable surface, as indicated at stage 33; and, the full-spectrum visible-light illumination and NIR radiation are carried-out at stage 34. Return of non-absorbed radiation, as reflected from wood-materials on the movable support surface, is indicated at stage 35. The selected range of wavelengths is monitored for return-reflected VIS/NIR radiation at stage 36. At stage 37, processing software, operating in accord with the above-described calibration method, removes the effect of moisture constituents and provides a percentage weight measurement responsive to the absorptive effect of resin-loading of the strand-wood material.

To evaluate and verify the calibration method, known resin-weight percentage levels for the test-samples were established as set forth above and were measured while moving at the selected rate. Those measurements with calibrated instrumentation, verified the linear relationship between resin-loading and spectral data, which enables meeting desired manufacturing standards, as exemplified graphically in FIG. 3 in which VIS/NIR measured resin-loading is plotted versus actual pre-established resin-loading, see tabulation below. Pre-established resin-loading percentage weights are presented along the "x" axis, reference number 38 of FIG. 3; resin-loading percentage weights, as measured by calibrated VIS/NIR spectroscopy, are set forth along the "y" axis, reference 39 of FIG. 3.

Figure 3:
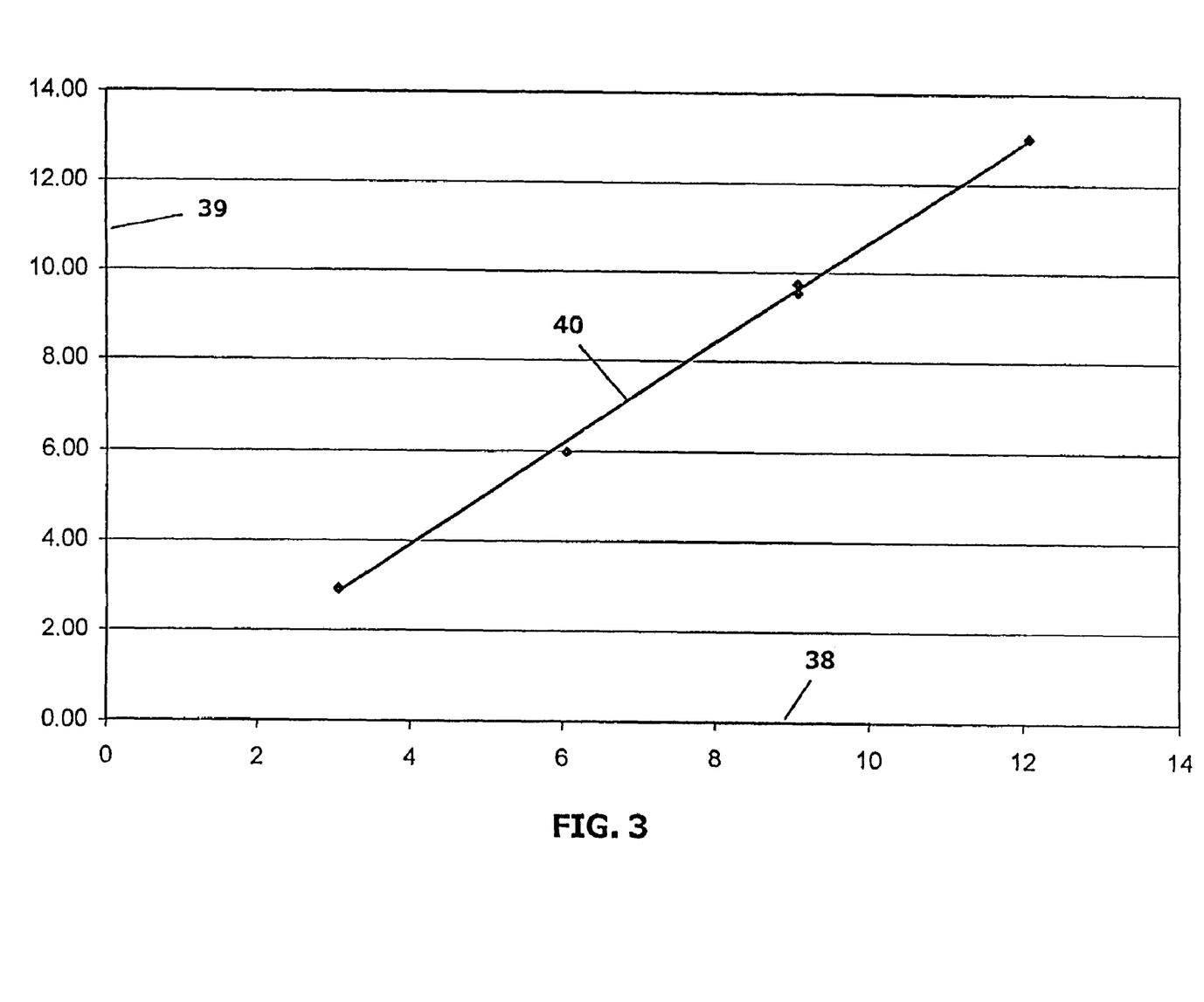
FIG. 3 is a graphical presentation verifying quantitative calibration results of VIS/NIR spectroscopic instrumentation in accordance with the invention.

Solid graph line 40 shows the algebraic linear relationship between resin-loading and spectral data; and, actual measurements are presented by the square markings.

TABULATION:

| Actual Resin Loading | VIS/NIR Measured Resin Loading |
|---|---|
| 3.07 | 2.93 |
| 3.07 | 2.91 |
| 6.06 | 5.99 |
| 9.08 | 9.55 |
| 9.08 | 9.75 |
| 12.08 | 13.04 |

The accuracy of resin-loading measurements is within manufacturing standards, when measured by calibrated VIS/NIR spectroscopic instrumentation as described in relation to FIGS. 1 and 2. That result confirms the calibration method based on removing the absorptive effects of moisture content.

Figure 4:
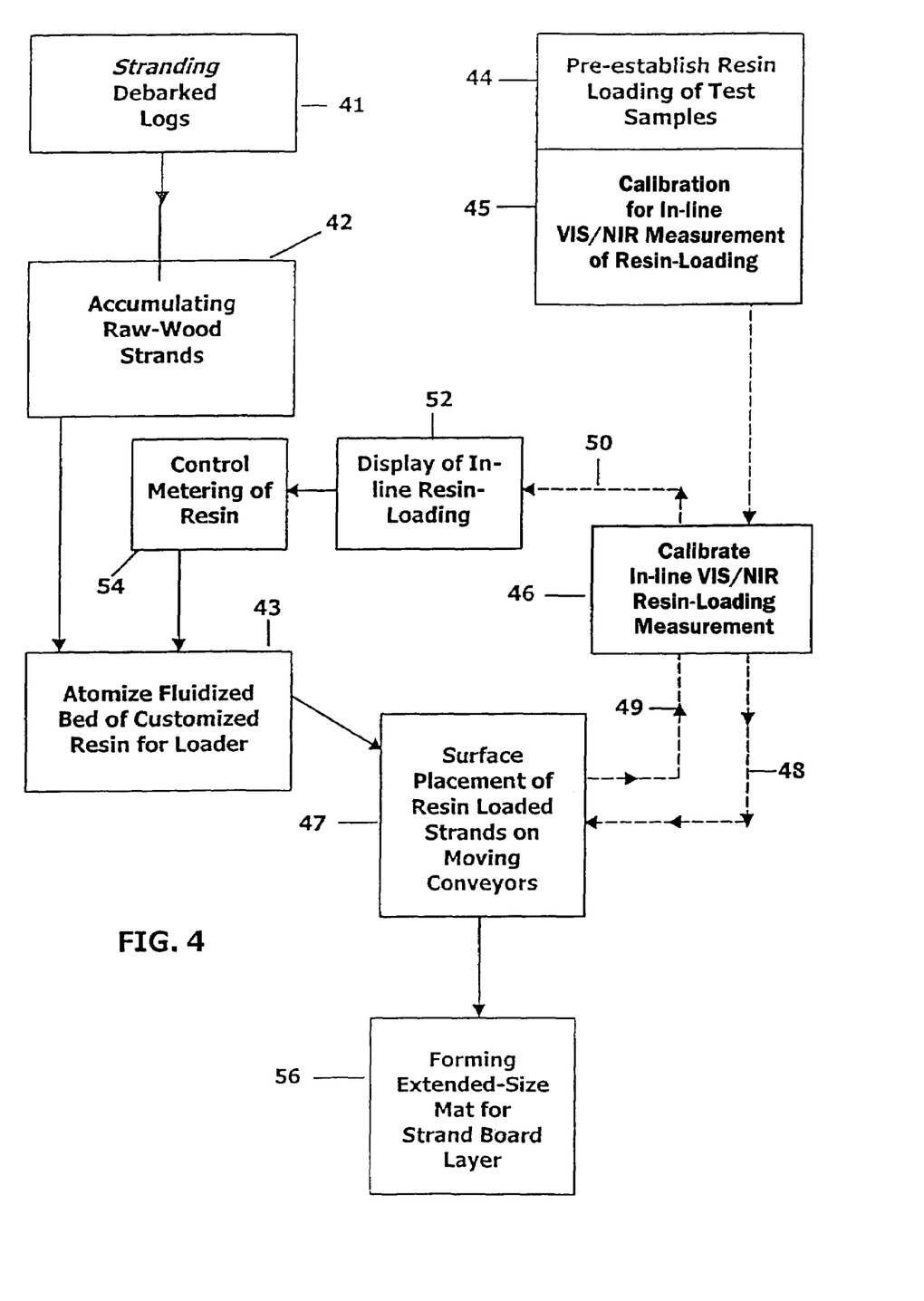
FIG. 4 is a flow chart for describing concepts for NIR spectroscopic calibration and correlating with on-line resin-loading operations for assembly of wood-materials, in accordance with the invention.

Correlating VIS/NIR spectroscopic measurement calibration technology with on-line assembly in a continuing manner is described in relation to FIG. 4. In that diagrammatic flow-chart wood-strand materials are formed into a specific individual strand-board layer, such as a face-layer of multi-layer oriented strand board (OSB). Debarked logs are strand-cut to dimensions, described above, at stage 41. The wood-strand material is accumulated at station 42 and directed for entry into, and for controlled in-line movement through resin-loading 43. A liquid phenolic can include powdered phenolic. However, phenolic resin in a liquid form, capable of being atomized, is preferred in the specific OSB embodiment disclosure of the invention. A controlled amount of powdered phenolic can be included in that embodiment.

Resin-loading for in-line assembly is carried out during passage through fluidized-bed resin-loading stage 43. On-line calibration of the instrumentation can be initiated at stage 44 of FIG. 4. The calibration processing as described in relation to FIGS. 1, 2 and 3 above, can be carried-out by combining stages 44 and 45. That is, test-samples of known resin-loading are established at station 44; the described calibration method, involving removal of moisture content spectra for providing prompt on-line NIR measurement of resin-loading, within manufacturing standards, can be provided on-line and periodically verified. Calibrated VIS/NIR instrumentation measurement of resin-loading is carried out at in-line measurement station 46.

During assembly, resin-loaded wood strands, from fluidized bed 43, are placed on an in-line conveyor surface at station 47. Said conveyor is moving at a rate coordinated with the controlled-rate of movement of wood-material, through fluidized-bed resin-loading station 43. Resin-loaded wood strands, moving on the conveyor-surface of station 47, are illuminated by visible-light and irradiated by VIS/NIR source are directed, as indicated by interrupted line 48, from measurement station 46. And, return-reflected VIS/NIR energy is directed along interrupted line 49 for calibrated VIS/NIR instrumentation measurement of resin-loading at measurement station 46.

Use of the calibration method, as described, enables measurement of resin content during assembly-line linear movement of wood-material of unknown moisture levels and unknown resin percentage weight. In calibration method return-reflected VIS/NIR energy is directed, as indicated by interrupted line 49, for removal of absorptive effects, of moisture spectra at station 46. The resulting calibrated-measurement of resin loading weight is directed, as indicated by interrupted line 50, for display at station 52. In FIG. 4, resin-loading of the individual wood strand layer is measured in-line, on a moving conveyor, and is displayed at station 52.

The resin-loading data of display station 52 enables control of desired resin-loading during on-line assembly. Metering of prepared resin can be carried out at station 54. Resin-loading for wood strands, for forming a face-layer of an oriented-strand board (OSB), can be selected, for example, at a weight of three percent (3%); in that example: resin-loading by weight is 3% of the wood-strand material moving through fluidized bed resin-loading station 43. The resin-loading value display at station 52 enables control of resin-loading of the wood strand while moving at a controlled rate through resin-loading-bed 43. A selected rate of resin-loading, can be maintained utilizing proper resin metering at metering station 54 and/or proper movement of the wood-strand material through fluidized bed resin-loading stage 43.

During line operations, observing the calibrated VIS/NIR spectroscopic quantitatively measured resin-loading data at station 52, enables diminishing or increasing the metering rate of the resin at station 54; or, diminishing or increasing the movement rate of the wood at fluidized-bed resin-loading station 43, in order to maintain a continuing desired resin-loading value for in-line assembly of a strand-layer. The prompt and accurate measurement, with display of resin-loading, enables on-line control which helps to maintain continuing assembly within manufacturing standards.

Figure 5:
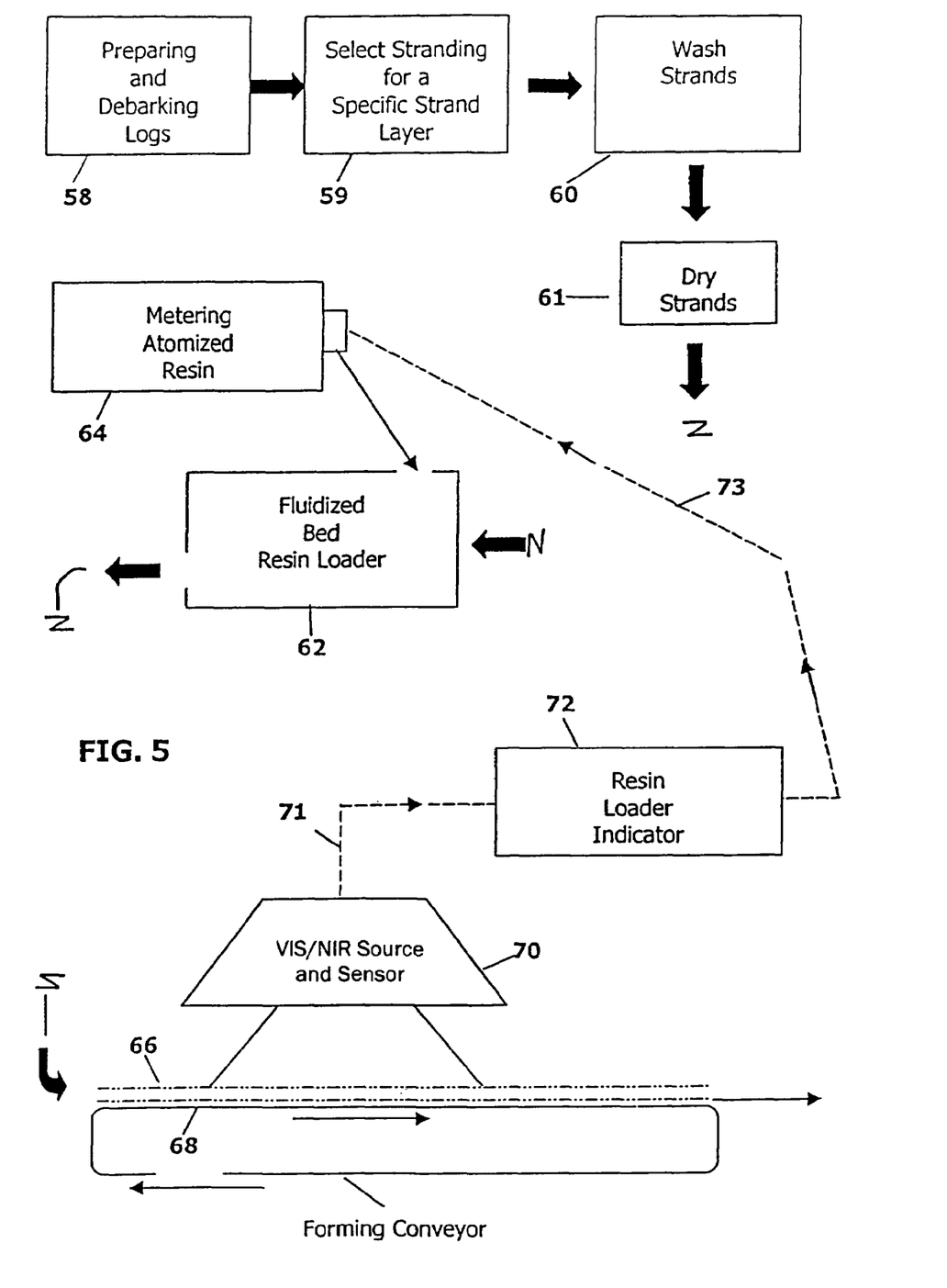
FIG. 5 is a diagrammatic presentation for describing on-line equipment for preparing and handling wood-strand materials and carrying out on-line resin-loading of those wood-materials using calibrated VIS/NIR spectroscopic quantitative-analyses of the invention, including use of feed-back information, as measured on-line, for maximizing continuing resin-loading within desired manufacturing specifications.

FIG. 5 is presented for describing the type of equipment utilized for forming, on-line, an individual strand-layer for oriented strand-board (OSB). Prepared and debarked logs, from station 58, are directed for selected stranding for a strand-layer, at stage 59. Preferably, strands are washed at 60; and, are at least partially dried for accumulation at station 61 for in-line usage. Strands are directed at a controlled-rate, measured in weight of strands per unit time, for in-line movement through a fluidized resin-loader 62.

Phenolic resin is prepared for metering at station 64. Metering is controlled to maintain a selected resin percentage weight, which can be about three percent (3%) of the weight of wood strands for a face layer of oriented strand board (OSB). The movement rate of wood strand through resin-loader 62, as measured in weight per unit time, can be increased or decreased as correlated with the resin metering rate. Liquid phenol-formaldehyde (PF) is atomized in a specific embodiment of the invention. Resin-loader 62 defines a specific internal volume for a fluidized-bed of resin; strands from station 61 are directed into, through, and out of resin-loader 62 at an in-line controlled rate which is measured in terms of movement of a specific weight of strands per unit time.

A tumbling action for thin strands in resin-loader 62 facilitates uniform resin-loading of individual strands with atomized resin from metering station 64, as resin is introduced at controlled rate correlated with movement rates of the strands. The strand movement rate can be maintained at a constant level during operations by control of the resin-metering rate.

From resin-loader 62, the resin-loaded wood strands are directed for forming strand layer 66; that layer is indicated by interrupted lines, on the moving surface of forming conveyor 68. VIS/NIR source and sensor head 70 provide for illuminating the strand-layer as assembled and for irradiating with VIS/NIR in a selected range of wavelengths. Reflecting non-absorbed radiation is measured at calibrated sensor 70 and that measurement is directed, as indicated by interrupted line 71, to resin-loading indicator 72. That indicated value is used for control of resin-loading should an indicated value vary from a selected desired resin-loading; for example, by feedback control over interrupted line 73 to resin metering station 64.

Figure 6:
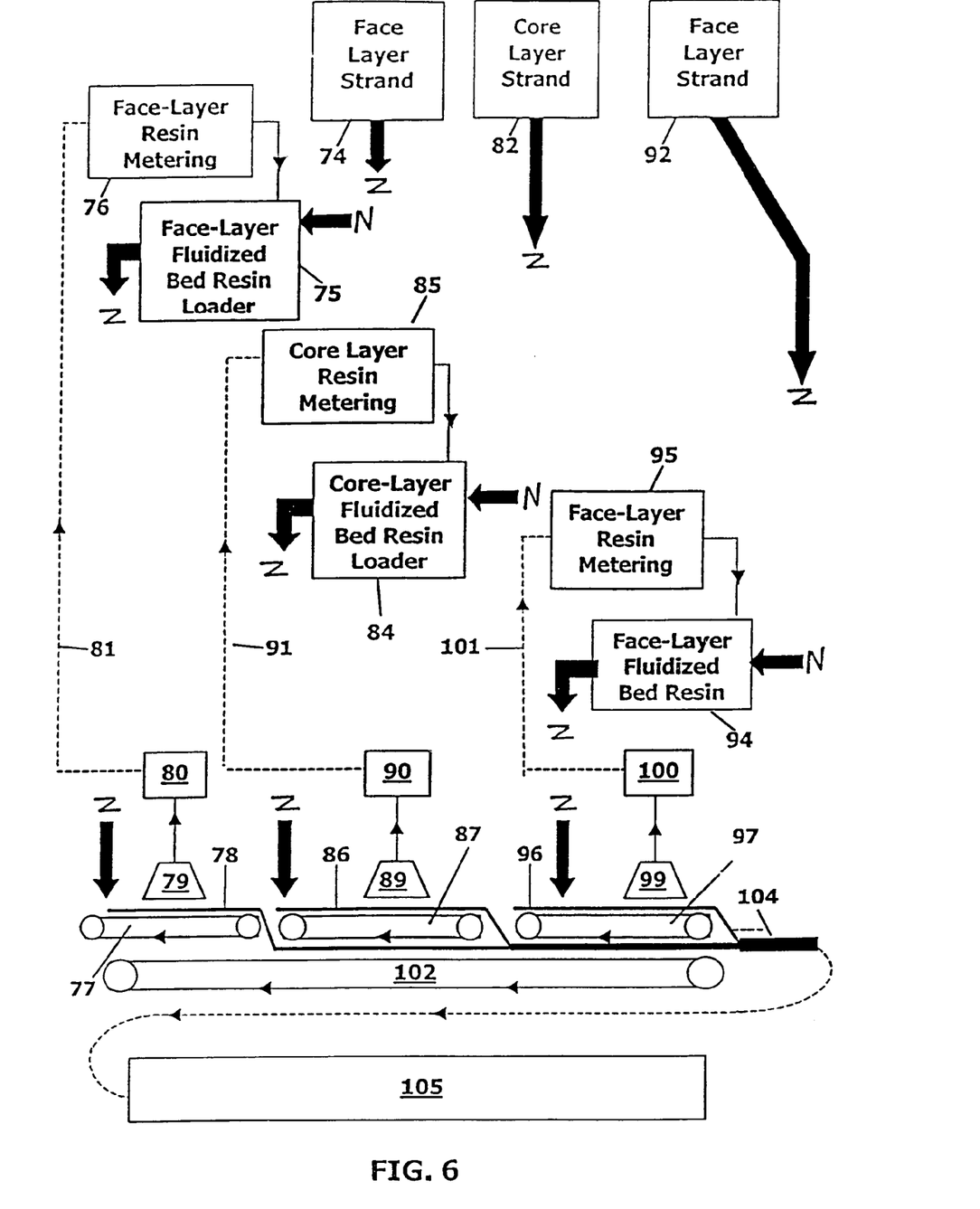
FIG. 6 is a schematic view for describing control of resin-loading of distinct individual wood strand layers, in accordance with the invention, for completing subsequent bonding of composite oriented-strand-board.

Steps and equipment for multiple-layer OSB specific embodiment of the invention are described in relation to FIG. 6; in which individual layers of the multiple layers selected, are assembled and directed for bonding into composite oriented strand board. Individual strand layers can differ in thickness, and other aspects, as tabulated later herein. The face layers, located on opposite planar surfaces of a centralized core layer, can include a wax for moisture resistance; also, the resin selected for the core layer can differ from that for the face layers.

Face layer strand is fed from station 74 of FIG. 6, at a controlled rate, in weight per unit time, into fluidized-bed resin loader 75 which defines a volume for feeding at a specified rate. Resin is metered at a controlled rate from station 76, to achieve desired resin-loading, within a desired manufacturing specifications. Resin-loaded strands are directed to first conveyor 77 forming resin-loaded face-strand layer 78. That resin-loading is measured by visual (VIS) and near infrared (NIR) spectroscopic equipment 79, which is calibrated as described above. Resin-loaded percentage weight is directed to display 80. Feedback signal-line 81 provides for promptly correcting percentage resin-metering to maintain manufacturing specifications.

Strands for central core layer are directed from station 82, as indicted, to core-layer fluidized-bed resin-loader 84. The resin for the core layer can differ from the phenol-formaldehyde used for the face-layers; as set forth later. Core-layer resin is metered at station 85 and directed, as indicated to resin-loader 84, so as to maintain resin-loading metering within manufacturing specifications.

Resin-loaded core strands are directed, as indicated, from station 84, to form core-strand layer 86 on the moving surface of conveyor 87. Resin-loading for the core layer 86 is measured by calibrated VIS/NIR spectroscopic equipment 89, as described earlier; and, the percentage weight is displayed at indicator 90. Feedback line 91, to core-resin metering station 85, enables any deviation from a desired core resin percentage weight to be corrected promptly.

Simultaneously, with forming of the above-described face layer and core layer, strand for a remaining face strand layer is directed from station 92, as indicated, to face-layer fluidized-bed resin loader 94, which provides for in-line movement of strand at a selected controlled rate. Face-layer resin metering is carried out at station 95. Resin-loaded strands are directed, as indicated, to form face-layer 96 on conveyance surface 97, which is moving as indicated.

Resin-loading of face layer 96 is quantitatively analyzed by calibrated VIS/NIR spectroscopic equipment 99; that percentage weight measurement result is directed to display 100, as indicated, correction of percentage weight resin-loading, if required, can be promptly directed via feedback line 101 to metering station 95; for maximizing production within desired standards.

Assembly of the individual strand layers is carried out via the individual moving conveyors 77, 87, and 97. Resin-loaded face strand layer 78, moves from conveyor 77 to conveyor surface 102, moving as indicated. The core strand layer 86 moves onto the face-layer being conveyed by conveyor surface 102, as indicated. And, the remaining face layer 96 moves onto the remaining surface of the core layer 86. The three resin-loaded layers are combined as conveyor 102 and indicated at 104 of FIG. 6; the multiple assembled layers are directed to station 105 for bonding utilizing heat and pressure values, as tabulated later herein.

Figure 7:
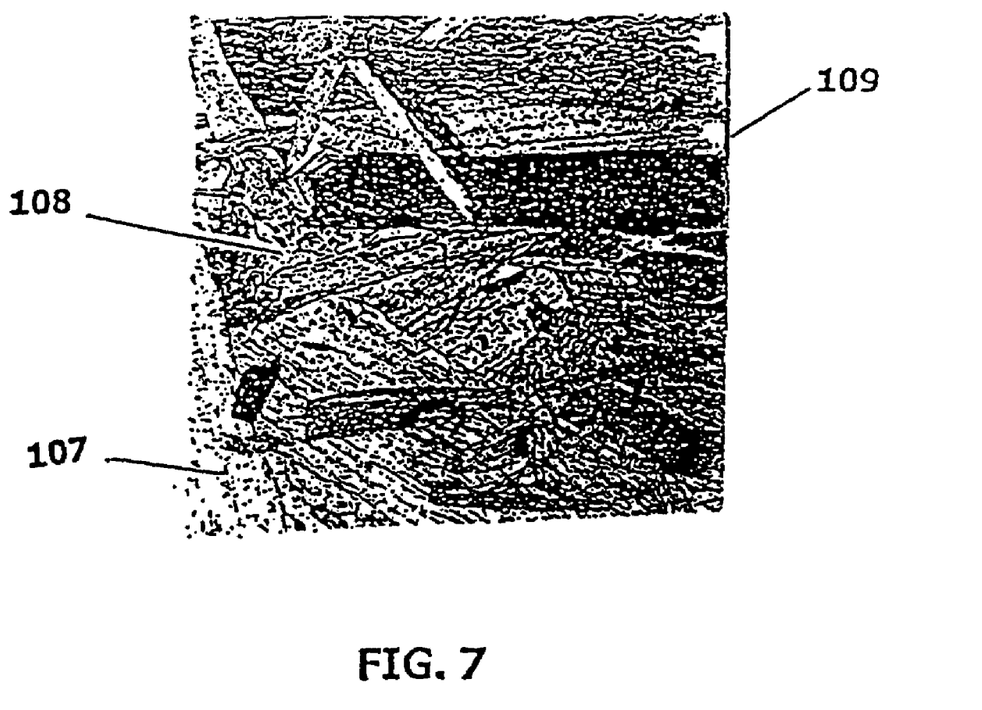
FIG. 7 is a top plan view for describing an external face surface of OSB as assembled using VIS/NIR spectroscopic measurement of resin-loading in accordance with the invention.
Figure 8:
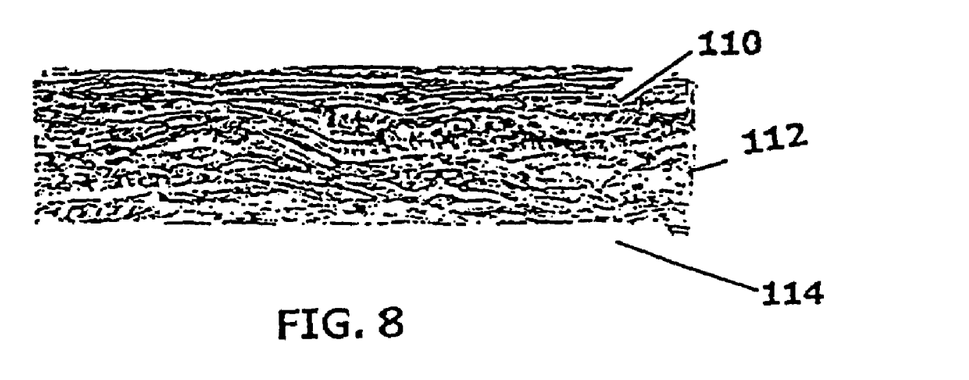
FIG. 8 is a front-elevation view of the OSB of FIG. 7, for describing assembly of resin-loaded individual wood-strand layers in accordance with the invention, as subsequent pressed and bonded to produce composite oriented-strand-board of the invention.

The number of layers in oriented strand board (OSB) can be selected. FIGS. 7 and 8 present respectively a top plan view and a side elevation view of a sample portion of three-strand oriented strand board (OSB) as assembled in accordance with the invention, and bonded using heat and pressure.

The top plan view of FIG. 7 depicts the differing orientations of the elongated thin strands; note, for example, strand 107 and strand 108 in surface 109. The front-elevation view of FIG. 8 depicts thickness of face layer 110, central core layer 112, and remaining face layer 114. The strands of the central core layer 112 can be selectively oriented in-line with the elongated dimension of assembly; that is, strands in a central core can be selectively oriented more uni-directionally than in a face layer.

The multiple directional orientations of elongated thin strands of the multiple layers contribute to structural strength characteristics of the OSB; and, help to prevent bending during use, for example, of four by eight (4'×8') panels extending between structural supports. Control of resin-loading, during assembly, as described above, helps to provide an engineered composite wood-strand product with consistent high-strength properties for structural uses. OSB thickness (shown in FIG. 8) can be selected in a range of above about one fourth inch (above about seven mm) to about three quarters inch (nineteen mm); as set forth in the following tabulated data.

TABLE

ORIENTED STRAND BOARD

| | |
|---|---|
| Overall thickness | above ¼" to about ¾" (about 0.7 to about 19 mm) |
| Each Face Strand (thickness) | about 0.125" (0.635 mm) to about 0.1875" (4.445 mm) |
| Core Strand Layer Thickness | about 0.322" (8.1 mm) to about 0.45" (11.4 mm) |
| Face Strand Layer Resin (phenolic) | phenol-formaldehyde |
| Core Strand Layer Resin | isocyanates or phenolics |

Curing: Loose layers of the resin-loaded thin wood strands are compressed under pressure at temperature(s) of about 350° F. to 400° F. (177° C. to 204° C.), for about three to five minutes.

(1) Source for Spectroscopy Equipment:

Source: Analytical Spectral Devices, Inc. (ASD)
5335 Sterling Drive, Suite A
Boulder, Colorado 80301

TABLE-continued

| Instrument Name: | FIELDSPEC PRO |
| --- | --- |
| Sensors: | (Arranged in Increasing Order of Price) |
| Wavelength (nm) | Detection Type |
| 350-1050 | Silicon |
| 1000-1800 | Indium-Gallium-Arsenide; single spectrometer |
| 1000-2500 | Indium-Gallium-Arsenide; dual spectrometer |
| 350-2500 | Silicon + Indium-Gallium-Arsenide (photodiode array) |
| (2) Source: | Foss-NIR Systems<br>12101 Tech Road<br>Silver Spring, Maryland 20904 |
| Wavelength (nm) | Detection Type |
| 400-2500 | Lead Sulfide |
| Software Processing Equipment | |
| Source: | ASD<br>For collecting spectra data<br>Name: LabSpec PRO, version 6.0<br>For measured Data Processing<br>Name: Grams/32 V5 |
| Source For Resin: | Dynea USA, Inc.<br>1600 Valley River Drive<br>Suite 390<br>Eugene, Oregon 97401<br>USA |

Principles of the invention, as described in detail in relation to oriented strand board (OSB), also extend to assembly of other wood strand products. Another composite wood strand product, described below, is referred to as oriented-strand-lumber (OSL). Oriented-strand-lumber utilizes more precise stranding of elongated strands of increased thickness than those for oriented-strand board (OSB). For example, strands for OSL can have a thickness of about 0.4 inch to about 0.5 inch (about 10 mm to about 12.5 mm); and, spread-weight measuring of resin-loading is carried out in accordance with present principles.

Figure 9:
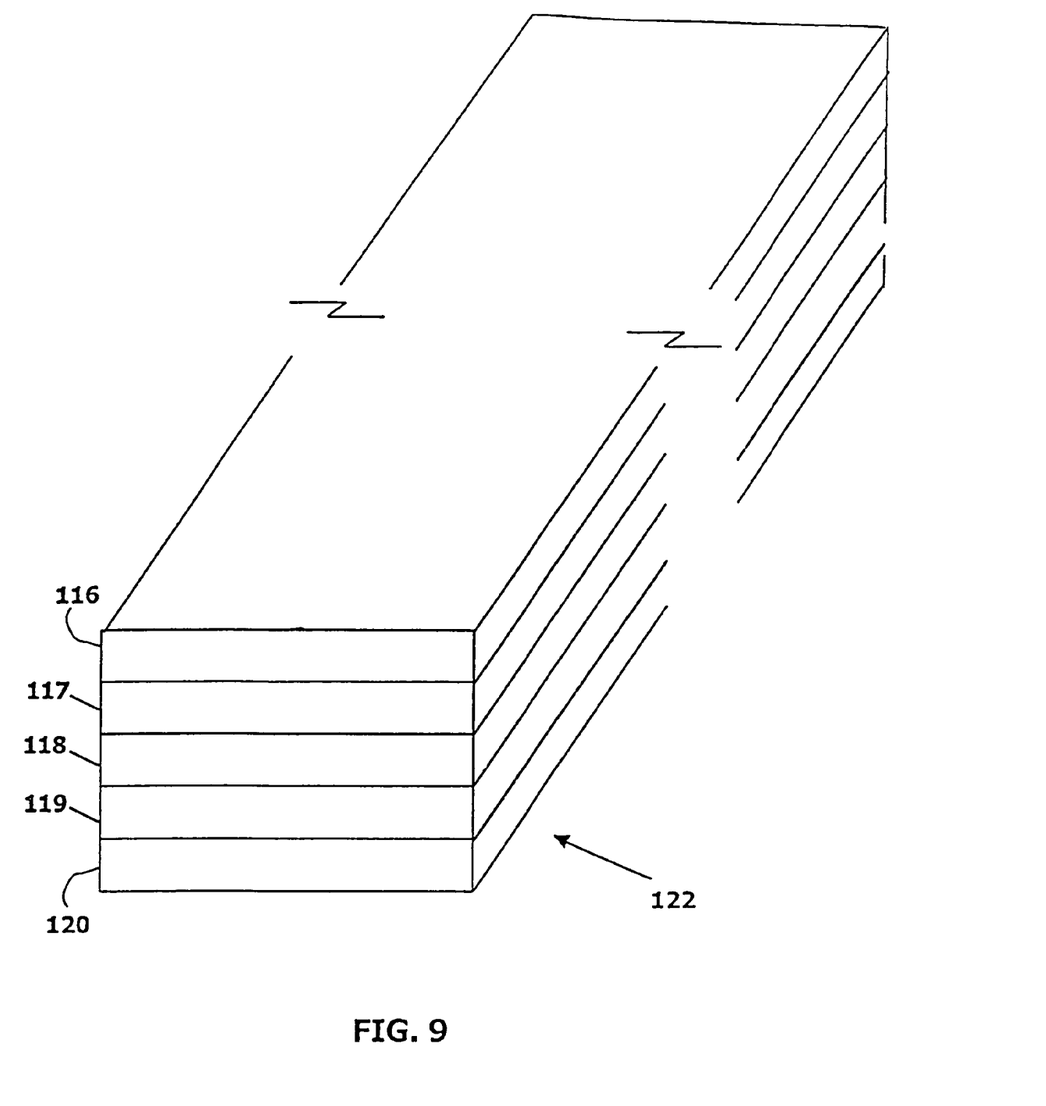
FIG. 9 is a perspective view for describing resin-loading using calibrated VIS/NIR spectroscopic technology and principles of the invention for producing oriented strand lumber.

FIG. 9 presents a perspective view of an end-usage product of bonded oriented strand lumber (OSL). OSL is assembled in an extended surface area mat from which various products can be cut during finishing. The bonded multiple strands of the finished product of FIG. 9, from top strand 116, through strands 117, 118 and 119, to bottom strand 120, include intermediate resin-loading, as measured and applied as spread weight, in accordance with principles of the invention. Use of the above-described calibrated VIS/NIR spectroscopic resin-loading principles provides for prompt measuring; and, helps to maintain uniformity of resin-loading spread weight for assembly of an extended surface-area mat, as set forth above.

FIG. 9 depicts a finished product, such as a "two by four" stud cut from an extended surface area mat. Five strand-lumber layers, with measured resin-loading are assembled in a large surface area mat, and then bonded by heat and pressure to form composite OSL. Four or five layers of strand lumber can be used in assembly of an extended area mat. A representative total thickness can be extended from about 1.75 inches (about 44.5 mm) to about two inches (about 50 mm). The thickness for an individual strand lumber layer can be about 0.35 inch (about 9 mm) to about 0.4 inch (about ten mm).

Phenol-formaldehyde (PF) resins, are spray-coated on the strand lumber, and measured for resin spread-weight per unit area, for assembly of wood-strand lumber. Bonding is carried out in a temperature range as set forth earlier for phenolic. The length and width dimensions for individual lumber wood strands can be selected for particular end usage; and strands can be inter-fitted in forming an extend surface-area mat. After bonding, finish end-usage product can be cut, such as studs and millwork.

Specific materials, dimensions, percentages, and other values have been set forth for purposes of describing specific embodiments which enable one skilled in the art to make and use the invention. However, it should be recognized that the above disclosures of embodiments include specific descriptions of materials, combinations, percentages, dimensions, and other values, which, in the light of the above disclosure, can enable one skilled in the art to make changes in those specified values, while continuing to rely on the principles of the invention as disclosed. Therefore, in evaluating valid patent coverage, for the disclosed subject matter, reference should be made to the appended claims; and, the language of those claims should be construed in the light of the above disclosures.

What we claim as our invention is:

1. Method for calibrating electromagnetic-radiation spectroscopic instrumentation so as to enable use in quantitative measurement of resin-loading of wood-materials during in-line assembly for subsequent bonding during production of a composite wood-product, comprising (A) providing electromagnetic-radiation spectroscopic instrumentation with a wavelength range for penetration of resin-loaded wood material;

(B) quantitatively pre-establishing resin-loading of reference-source test-samples of wood-materials of a type selected for in-line assembly, and capable of providing for bonding to produce a composite wood-product;

(C) supporting said pre-established resin-loaded test-samples on a conveyance surface capable of establishing a controlled rate of relative movement between said supported test-samples and said spectroscopic instrumentation for irradiating wood-materials of said test-samples;

(D) establishing said controlled rate of relative movement for said test-samples simulating a selected in-line controlled-rate of movement of resin-loaded wood-materials being directed in-line for assembly;

(E) irradiating said pre-established resin-content test-samples with a selected wavelength range of radiation during relative movement between said spectroscopic instrumentation and said test samples at a selected controlled rate for quantitative measurement of absorption of said selected wavelength range of radiation of said wood-materials of said pre-established resin-content test-samples, and (F) calibrating said spectroscopic instrumentation by providing a calibration curve enabling quantitative analyses of resin-loading of test-sample during said controlled movement of said test samples, by measuring non-absorbed radiation energy within said selected wavelength range of radiation as reflected by said exposed test-samples on said conveyance surface.

2. The invention of claim 1, wherein said selected wavelength range of radiation is selected from the group consisting of (1) 350-1050 nm, (2) 1000-1800 nm, (3) 1000-2500 nm, and (4) 400-2500 nm.

3. The invention of claim 1, including establishing resin-content of said test-samples so as to present an incrementally-progressive resin-loading for wood-materials of respective test-samples, with said resin-loading being selected from the group, consisting of (i) a spread weight per unit area, and (ii) percentage weight of resin to weight of wood materials, extending in a range of zero percent to about fourteen percent (14%).

4. Method for calibrating electromagnetic-radiation spectroscopic instrumentation so as to enable use in quantitative measurement of resin-loading of wood-materials during in-line assembly for subsequent bonding during production of a composite wood-product, comprising
  (A) providing electromagnetic-radiation spectroscopic instrumentation with a wavelength range for penetration of resin-loaded wood material;
  (B) quantitatively pre-establishing resin-loading of reference-source test-samples of wood-materials of a type selected for in-line assembly, and capable of providing for bonding to produce a composite wood-product;
  (C) supporting said pre-established resin-loaded test-samples on a conveyance surface capable of establishing a controlled rate of relative movement between said supported test-samples and said spectroscopic instrumentation for irradiating wood-materials of said test-samples;
  (D) establishing said controlled rate of relative movement for said test-samples simulating a selected in-line controlled-rate of movement of resin-loaded wood-materials being directed in-line for assembly;
  (E) irradiating said pre-established resin-content test-samples with a selected wavelength range of radiation during relative movement between said spectroscopic instrumentation and said test samples at a selected controlled rate for quantitative measurement of absorption of said selected wavelength range of radiation of said wood-materials of said pre-established resin-content test-samples, and
  (F) calibrating said spectroscopic instrumentation by providing a calibration curve enabling quantitative analyses of resin-loading of test-sample during said controlled movement of said test samples, by measuring non-absorbed radiation energy within said selected wavelength range of radiation as reflected by said exposed test-samples on said conveyance surface,
  wherein resin-content of said test-samples is established so as to present an incrementally-progressive resin-loading for wood-materials of respective test-samples, with said resin-loading being selected from the group, consisting of (i) a spread weight per unit area, and (ii) percentage weight of resin to weight of wood materials, extending in a range of zero percent to about fourteen percent (14%), and wherein relative movement is established between said test-samples and said radiation, including steps of selecting a rotatable conveyance surface capable of being driven at a rotational rate to simulate a selected in-line movement rate for resin-loading of said type wood-materials of test-samples during in-line assembly of said wood-materials, and for measuring reflected radiation energy from wood materials of said resin-loaded test-samples.

5. Method for calibrating electromagnetic-radiation spectroscopic instrumentation so as to enable use in quantitative measurement of resin-loading of wood-materials during in-line assembly for subsequent bonding during production of a composite wood-product, comprising
  (A) providing electromagnetic-radiation spectroscopic instrumentation with a wavelength range for penetration of resin-loaded wood material;
  (B) quantitatively pre-establishing resin-loading of reference-source test-samples of wood-materials of a type selected for in-line assembly, and capable of providing for bonding to produce a composite wood-product;
  (C) supporting said pre-established resin-loaded test-samples on a conveyance surface capable of establishing a controlled rate of relative movement between said supported test-samples and said spectroscopic instrumentation for irradiating wood-materials of said test-samples;
  (D) establishing said controlled rate of relative movement for said test-samples simulating a selected in-line controlled-rate of movement of resin-loaded wood-materials being directed in-line for assembly;
  (E) irradiating said pre-established resin-content test-samples with a selected wavelength range of radiation during relative movement between said spectroscopic instrumentation and said test samples at a selected controlled rate for quantitative measurement of absorption of said selected wavelength range of radiation of said wood-materials of said pre-established resin-content test-samples, and
  (F) calibrating said spectroscopic instrumentation by providing a calibration curve enabling quantitative analyses of resin-loading of test-sample during said controlled movement of said test samples, by measuring non-absorbed radiation energy within said selected wavelength range of radiation as reflected by said exposed test-samples on said conveyance surface,
  wherein resin-content of said test-samples is established so as to present an incrementally-progressive resin-loading for wood-materials of respective test-samples, with said resin-loading being selected from the group, consisting of (i) a spread weight per unit area, and (ii) percentage weight of resin to weight of wood materials, extending in a range of zero percent to about fourteen percent (14%), and wherein providing a calibration curve for said spectroscopic instrumentation, includes removing absorptive effects responsive to moisture content of said wood-materials and of said resin.

6. The invention of claim 5, including obtaining calibrated measurement, in a selected wavelength range of about 400 nm to about 2250 nm, of resin-content of said test-samples by removing measured non-absorbed reflected radiation energy at wavelengths of 900 nm to 1000 nm, 1450 nm to 1500 nm, and 1900 nm to 2000 nm.

7. Method for calibrating electromagnetic-radiation spectroscopic instrumentation for non-invasive measurement of resin-loading of wood-materials during movement in-line for assembly and subsequent bonding for production of composite wood-strand product, comprising the steps of
  (A) preparing said wood-materials by strand-cutting wood strands having a high length-to-thickness ratio and selected surface-area dimension parameters, for in-line resin-loading and subsequent production of composite wood-strand product;
  (B) providing electromagnetic-radiation spectroscopic measuring instrumentation including a sensor head and a source of VIS/NIR radiation, for irradiating said wood-materials, in a range of wavelengths selected within about 350 nm to about 2500 nm;
  (C) calibrating said VIS/NIR spectroscopic measuring instrumentation for use in quantitative analyses of resin-loading of said wood-materials during movement in an assembly line, by
    (i) preparing reference-source test-samples from said wood-materials, including:
      (a) pre-establishing resin-loading of said test-samples, (b) quantitatively pre-selecting resin-loading for said wood-materials providing an incrementally-increasing resin-loading of wood-materials of said test-samples within a selected resin-loading range, and (c) positioning said pre-established resin-loaded test-samples on a conveyor surface capable for use during assembly of said cut wood strand materials;

(D) positioning said spectroscopic measuring instrumentation, and said VIS/NIR source, for
  (i) irradiating said test-samples, and
  (ii) providing penetration of, and at least partial absorption by, said resin-loaded test-samples of said VIS/NIR radiation within said selected range of wavelengths; and (E) calibrating said spectroscopic instrumentation, by
  (i) measuring non-absorbed radiation energy as reflected by said wood-strand materials of said test-samples,
  (ii) comparing said calibrated absorbed radiation spectroscopic absorptive measurements of said incrementally-increasing pre-established resin-loading test-samples, with
  (iii) said pre-established resin-loading of wood-strand materials of said respective test-samples for verifying accurate calibrating of said instrumentation for measurement of resin-loading.

8. Method for calibrating electromagnetic-radiation spectroscopic instrumentation for non-invasive measurement of resin-loading of wood-materials during movement in-line for assembly and subsequent bonding for production of composite wood-strand product, comprising the steps of (A) preparing said wood-materials by strand-cutting wood strands having a high length-to-thickness ratio and selected surface-area dimension parameters, for in-line resin-loading and subsequent production of composite wood-strand product;

(B) providing electromagnetic-radiation spectroscopic measuring instrumentation including a sensor head and a source of VIS/NIR radiation, for irradiating said wood-materials, in a range of wavelengths selected within about 350 nm to about 2500 nm;

(C) calibrating said VIS/NIR spectroscopic measuring instrumentation for use in quantitative analyses of resin-loading of said wood-materials during movement in an assembly line, by
  (i) preparing reference-source test-samples from said wood-materials, including:
    (a) pre-establishing resin-loading of said test-samples,
    (b) quantitatively pre-selecting resin-loading for said wood-materials providing an incrementally-increasing resin-loading of wood-materials of said test-samples within a selected resin-loading range, and
    (c) positioning said pre-established resin-loaded test-samples on a conveyor surface capable for use during assembly of said cut wood strand materials;

(D) positioning said spectroscopic measuring instrumentation, and said VIS/NIR source, for
  (i) irradiating said test-samples, and
  (ii) providing penetration of, and at least partial absorption by, said resin-loaded test-samples of said VTS/NTR radiation within said selected range of wavelengths; and (E) calibrating said spectroscopic instrumentation, by
  (i) measuring non-absorbed radiation energy as reflected by said wood-strand materials of said test-samples,
  (ii) comparing said calibrated absorbed radiation spectroscopic absorptive measurements of said incrementally-increasing pre-established resin-loading test-samples, with
  (iii) said pre-established resin-loading of wood-strand materials of said respective test-samples for verifying accurate calibrating of said instrumentation for measurement of resin-loading,
in which step (E) includes selectively removing absorptive effects of radiation due to moisture-content of said wood test-samples and of said resin.

9. The invention of claim 8, further including
(F) providing for on-line use of said calibrated electromagnetic-radiation spectroscopic measuring instrumentation for non-invasive measuring of resin-loading of wood-strand materials moving in an assembly line for subsequent bonding-treatment production of composite wood-strand product, selected from the group consisting of (i) oriented strand board, and (ii) oriented strand lumber.

10. The invention of claim 7, in which
(G) controlling resin-loading is carried out by selection from the groups consisting of
  (i) quantitatively-controlling metering of resin as introduced for contact with said wood-strand materials,
  (ii) controlling rate of movement of said wood-strand materials in said assembly line, and
  (iii) combinations of (i) and (ii).

11. The invention of claim 9 for production of oriented strand board (OSB), carried out by controlling rate of movement of said wood-strand materials through a resin-loading structure, and correlating introduction of resin with rate of movement of said wood-strand materials so as to control resin-loading weight.

12. The invention of claim 11, further including
(H) establishing a rate of movement for resin-loaded wood-strand materials onto a strand-layer forming conveyor surface which is moving at a rate correlated with said calibrated spectroscopic instrumentation for measurement of resin-loading;
(I) utilizing said calibrated spectroscopic instrumentation for quantitatively-monitoring resin-loading of wood-strand materials, by
  (i) measuring resin-loading of said resin-loaded wood-strand materials, as delivered from said resin-loading structure, while moving on said strand-layer-forming conveyor, and
  (ii) indicating said measured resin-loading of raw said wood-strand materials so as to be available for control of assembly operations for purposes of controlling resin-loading.

13. The invention of claim 12, further including:
(J) providing for quantitative-control of said resin-loading, by
  (i) indicating resin-loading value as measured by said calibrated instrumentation, for
  (ii) feedback control of resin-loading, by
  (iii) selecting from the group consisting of
    (a) quantitatively controlling resin as introduced for contact with said strand materials,
    (b) controlling rate of movement of said strand materials being delivered for said assembly line, and
    (c) combinations of (a) and (b), for
  (iv) maintaining a desired uniform resin-loading weight in relation to weight of said wood-strands during strand layer forming assembly.

14. The invention of claim 13, including providing multiple separate movable strand-layer conveyor assembly surfaces for assembly of planar strand layers selected from the group consisting of (i) three-strand layers, and (ii) five-strand layers.

15. The invention of claim 14, for assembly of oriented strand board of three-strand layers, each strand layer receiving wood-strand materials at a controlled rate for separately forming (i) a face layer, (ii) a core-layer, and (iii) a remaining face layer.

16. The invention of claim 15, further including selecting respective resin and resin-loading percentage weight for each said separate layer; controlling resin-loading for each said separate strand-layer while moving on its respective conveyor surface, and combining said multiple planar layers by:
(i) positioning a resin-loaded face layer on each planar surface of said centrally-located resin-loaded core-layer, for
(ii) pressing said combined wood-strand layers by timed exposure to heat and pressure, for
(iii) polymerizing said controlled resin-loaded combined layers, producing said composite oriented wood board.

17. The invention of claim 8 for production of oriented strand lumber (OSL), comprising selecting strand lumber having a high length-to-thickness ratio, controlling resin-loading of said strand lumber using electromagnetic-radiation calibrated spectroscopic measurement of resin loading, combining said resin-loaded strand lumber forming an enlarged mat for pressing under heat and pressure, and finishing said bonded mat by cutting said mat into end-usage product selected from the group consisting of (a) structural studs, and (b) millwork components.

* * * * *